United States Patent [19]

vor der Brück et al.

[11] 4,377,518
[45] Mar. 22, 1983

[54] AZO DYESTUFFS DERIVED FROM POLYCYCLO-HETERCYCLIC COUPLER COMPONENTS

[75] Inventors: Dieter vor der Brück, Bonn; Hans-Joachim Kabbe, Leverkusen, both of Fed. Rep. of Germany

[73] Assignee: Bayer Aktiengesellschaft, Leverkusen, Fed. Rep. of Germany

[21] Appl. No.: 183,872

[22] Filed: Sep. 3, 1980

[30] Foreign Application Priority Data

Sep. 4, 1979 [DE] Fed. Rep. of Germany ....... 2935720

[51] Int. Cl.³ .................. C09B 29/36; 307C 107/04
[52] U.S. Cl. .................. 260/156; 260/153; 260/154; 260/155; 544/245; 546/52; 546/89; 549/349; 549/402
[58] Field of Search ............ 260/156, 152, 153, 154, 260/155, 157

[56] References Cited

U.S. PATENT DOCUMENTS

| | | | |
|---|---|---|---|
| 2,130,016 | 9/1938 | Kranzlein et al. | 260/152 |
| 2,448,869 | 9/1948 | Dickey et al. | 260/155 X |
| 3,804,823 | 4/1974 | Fisher et al. | 260/154 |
| 4,260,540 | 4/1981 | Rolf et al. | 260/154 X |
| 4,294,755 | 10/1981 | Kanter | 260/154 |

FOREIGN PATENT DOCUMENTS

| | | | |
|---|---|---|---|
| 2036776 | 7/1980 | Fed. Rep. of Germany | 260/152 |
| 396255 | 1/1966 | Switzerland | 260/154 |

Primary Examiner—Charles F. Warren
Assistant Examiner—Margaret B. Medley
Attorney, Agent, or Firm—Sprung, Horn, Kramer & Woods

[57] ABSTRACT

Dyestuffs of the formula

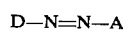

D—N=N—A      I in which
 D represents the radical of a diazo component and
 A represents the radical of a coupling component of the formulae

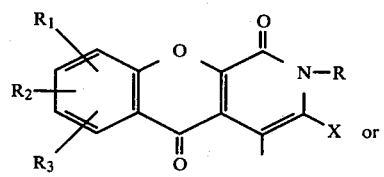

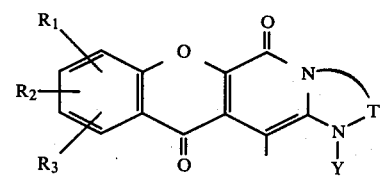

wherein
 $R_1$, $R_2$ and $R_3$ designate hydrogen or non-ionic radicals,
 R designates hydrogen or an optionally substituted alkyl, cycloalkyl, aryl, aralkyl or heterocyclic radical,
 X designates OH or

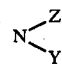

T designates the remaining members of a fused-on ring and
Y and Z designate hydrogen, optionally substituted alkyl or optionally substituted aryl,
processes for their preparation and process for pigmenting organic material using the dyestuffs of the formula I.

8 Claims, No Drawings

AZO DYESTUFFS DERIVED FROM POLYCYCLO-HETERCYCLIC COUPLER COMPONENTS

The invention relates to azo dyestuffs of the formula $$D-N=N-A \quad (I)$$

in which
D represents the radical of a diazo component and
A represents the radial of a coupling component of the formulae

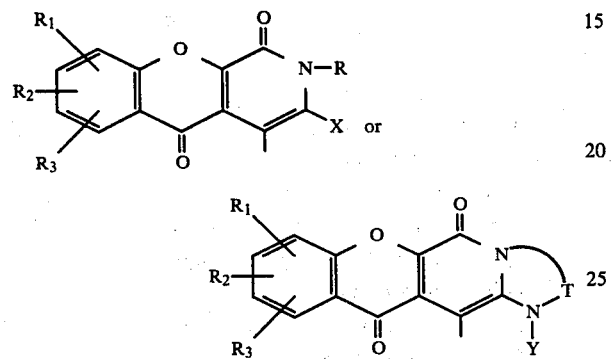

wherein
$R_1$, $R_2$ and $R_3$ designate hydrogen or non-ionic radicals,
R designates hydrogen or an optionally substituted alkyl, cycloalkyl, aryl, aralkyl or heterocyclic radical,
X designates OH or

T designates the remaining members of a fusedon ring and
Y and Z designate hydrogen, optionally substituted alkyl or optionally substituted aryl.

In the formula,
D preferably represents the radical of a diazo component of the benzene, naphthalene, anthraquinone or heterocyclic series, it being possible for the phenyl, naphthyl, anthraquinonyl or heterocyclic radicals of the diazo component to be substituted, for example by nitro, cyano, halogen, preferably chlorine or bromine, carbamoyl or sulphamoyl, it being possible for the carbamoyl and sulphamoyl radicals to be mono-substituted or disubstituted by $C_1$-$C_4$-alkyl, benzyl, phenethyl or phenyl, which in its turn can be further substituted by chlorine, bromine, $C_1$-$C_4$-alkyl and $C_1$-$C_4$-alkoxy, alkylsulphonyl, preferably $C_1$-$C_4$-alkysulphonyl, arylsulphonyl, preferably phenyl- or naphthyl-sulphonyl, alkoxy, preferably $C_1$-$C_8$-alkoxy, aryloxy, preferably phenoxy, alkyl, preferably $C_1$-$C_8$-alkyl, alkoxycarbonyl, preferably $C_1$-$C_8$-alkoxy-carbonyl, trifluoromethyl, acylamino, preferably $C_1$-$C_4$-alkycarbonylamino, benzoylamino which is optionaly substituted by chlorine, methyl, methoxy or ethoxy, phenylacetylamino, $C_1$-$C_4$-alkylaminocarbonylamino, phenylaminocarbonylamino, phenoxycarbonylamino or s-triazinylamino, it being possible for the s-triazinyl radical to be substituted by Cl, Br, F or $C_1$-$C_4$-alkoxy, examples of heterocyclic radicals D which may be mentioned being:

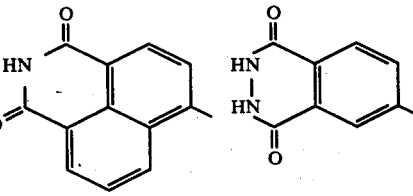
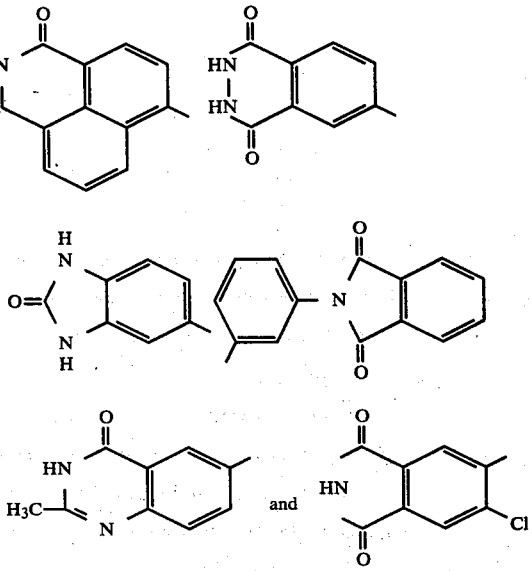

$R_1$, $R_2$ and $R_3$ preferably represent hydrogen, alkyl, preferably $C_1$-$C_4$-alkyl, halogen, preferably chlorine or bromine, alkoxy, preferably $C_1$-$C_4$-alkoxy, carbamoyl, sulphamoyl, aryloxy, preferably phenoxy, alkoxycarbonyl, preferably $C_1$-$C_4$-alkoxycarbonyl, alkylsulphonyl, preferably $C_1$-$C_4$-alkylsulphonyl, arylsulphonyl, preferably phenylsulphonyl or naphthylsulphonyl, aryl preferably phenyl or naphthyl, acylamino, preferably $C_1$-$C_4$-alkyl-carbonylamino, benzoylamino which is optionally substituted by chlorine, methyl, methoxy or ethoxy, phenylacetylamino, $C_1$-$C_4$-alkylaminocarbonylamino, phenylaminocarbonylamino, phenoxycarbonylamino, nitro or cyano; R preferably represents hydrogen, $C_1$-$C_8$-alkyl which is optionally substituted by $C_1$-$C_4$-alkoxy, mono- or di-$C_1$-$C_4$-alkyl-amino, carbamoyl, sulphamoyl, acylamino, preferably $C_1$-$C_4$-alkylcarbonylamino, benzoylamino, phenylacetylamino, ($C_1$-$C_4$-alkyl)-carbonylamino, phenylaminocarbonylamino or phenoxycarbonylamino, it being possible for benzoylamino in its turn to be further substituted by chlorine, methyl, methoxy or ethoxy; or phenyl or naphthyl which is optionally substituted by $C_1$-$C_4$-alkyl, $C_1$-$C_4$-alkoxy, phenoxy, halogen, preferably chlorine or bromine, carbamoyl or acylamino, preferably $C_1$-$C_4$-alkylcarbonylamino or benzoylamino; or a cyclopentyl or cyclohexyl radical which is optionally substituted by phenyl, which can be substituted by halogen, preferably chlorine or bromine, $C_1$-$C_4$-alkyl or $C_1$-$C_4$-alkoxy, or by $C_1$-$C_4$-alkoxy, carbamoyl, preferably $C_1$-$C_4$-alkylcarbonylamino, benzoylamino which is optionally substituted by chlorine, methyl, methoxy or ethoxy, phenylacetylamino, ($C_1$-$C_4$-alkyl)-carbonylamino, phenylaminocarbonylamino or phenoxycarbonylamino; or benzyl or phenethyl which is optionally substituted by halogen, preferably chlorine or bromine, $C_1$–$C_4$-alkyl or $C_1$–$C_4$-alkoxy in the phenyl radical; or designates a radical

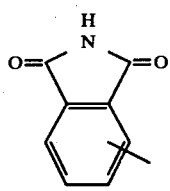

T designates the remaining members which are necessary to form a 5-membered or 6-membered saturated or unsaturated ring which includes the two N atoms already present;

Y and Z designate hydrogen, an optionally substituted $C_1$–$C_4$-alkyl radical, an optionally substituted phenyl radical or an optionally substituted naphthyl radical, the substituents of these radicals corresponding to those above for R in the meaming of optionally substituted $C_1$–$C_8$-alkyl, optionally substituted phenyl or optionally substituted naphthyl, and T preferably designates a divalent radical of the formulae

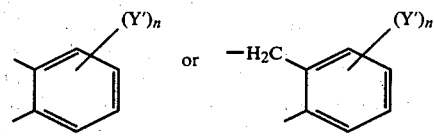

wherein

Y' represents a substituent, such as, for example, chlorine, bromine, nitro, cyano, $C_1$–$C_4$-alkyl or carbamoyl, and n designates 0, 1, 2 or 3.

Preferred dyestuffs correspond to the formula

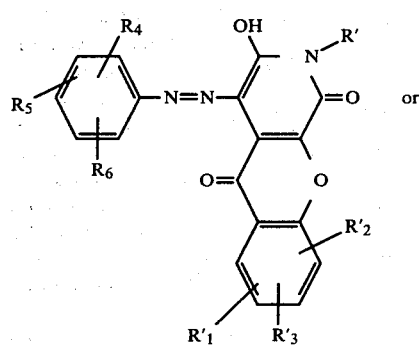

-continued-

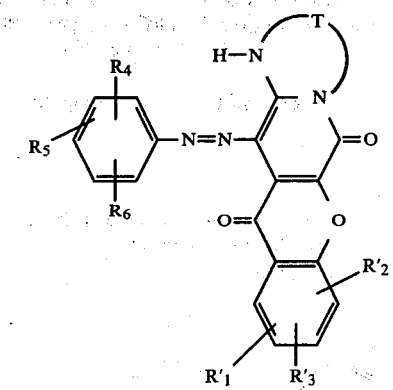

wherein

T has the abovementioned meaning,

R' represents hydrogen, $C_1$–$C_8$-alkyl which can be substituted by Cl, Br, $C_1$–$C_4$-alkoxy or (mono-$C_1$–$C_4$- or di-$C_1$–$C_4$-alkyl)-amino, phenyl which can be substituted by Cl, Br, $C_1$–$C_4$-alkyl, $C_1$–$C_4$-alkoxy, phenoxy which is optionally substituted by Cl, Br, methyl or nitro, nitro, carbamoyl, sulphamoyl, benzoylamino, acetylamino or phthaloylamino, benzyl or phenethyl which can be substituted in the phenyl radical by Cl, Br, methoxy, ethoxy, methyl or nitro, cyclohexyl or a radical

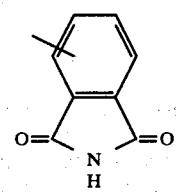

$R_1'$ and $R_2'$ represent hydrogen, methyl, chlorine, bromine, methoxy, ethoxy or phenoxy, $R_3'$ designates hydrogen, acetylamino, benzoylamino or methyl and $R_4$, $R_5$ and $R_6$ represent hydrogen, chlorine, bromine, methyl, methoxy, ethoxy, phenoxy, trifluoromethyl, nitro, $C_1$–$C_4$-alkyl, cyano, acetylamino, benzoylamino which is optionally substituted by Cl, or sulphamoyl or carbamoyl, it being possible for the sulphamoyl and carbamoyl radicals also to be monosubstituted or disubstituted by phenyl, which can in its turn be further substituted by chlorine, methoxy, ethoxy or methyl, or by benzyl, phenethyl and/or $C_1$–$C_4$-alkyl, or $C_1$–$C_4$-alkylsulphonyl, phenylsulphonyl, phenylaminocarbonyl and/or phenylaminocarbonylamino.

Further preferred dyestuffs correspond to the formulae

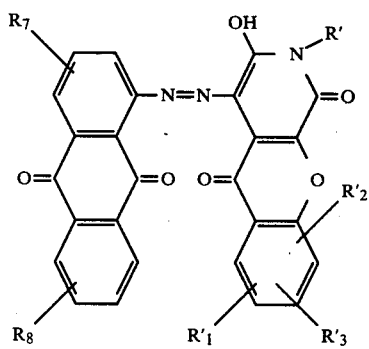

and

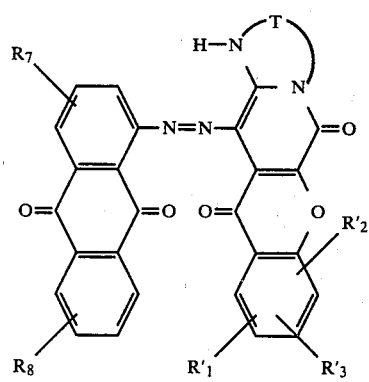

in which

T, R', R$_1$', R$_2$' and R$_3$' have the abovementioned meaning and

R$_7$ and R$_8$ represent hydrogen, C$_1$-C$_4$-alkyl, chlorine, bromine, benzoylaminocarbonylamino, C$_1$-C$_4$-alkylaminocarbonylamino, C$_1$-C$_4$-alkylcarbonylamino, phenylaminocarbonylamino, benzoylamino which is optionally substituted by chlorine, bromine, C$_1$-C$_4$-alkyl or C$_1$-C$_4$-alkoxy, or phenylsulphonylamino.

Particularly preferred dyestuffs correspond to the formulae

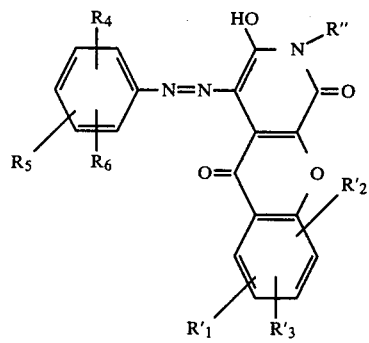

and

-continued

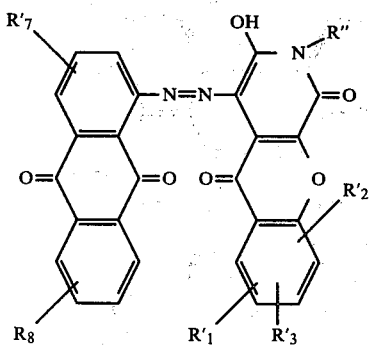

in which

R$_1$', R$_2$', R$_3$', R$_4$, R$_5$, R$_6$ and R$_8$ have the abovementioned meaning, R'' represents hydrogen, C$_1$-C$_4$-alkyl, phenyl, benzyl or phenethyl, it being possible for the phenyl radicals in phenyl, benzyl and phenethyl to be substituted by chlorine, bromine, methoxy, ethoxy, phenoxy, aminocarbonyl, acetylamino or benzoylamino, or phthalylamino or a radical of the formula

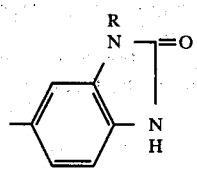

and

R$_7$' designated hydrogen, methyl, methoxy, ethoxy, nitro, (C$_1$-C$_4$-alkyl)-carbonylamino, benzoylamino or hydrogen.

Very particularly preferred dyestuffs correspond to the formulae

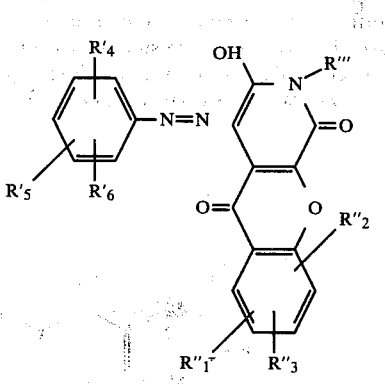

and

-continued

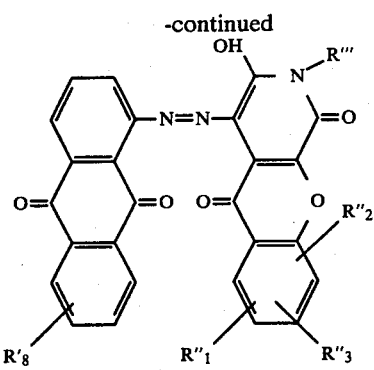

wherein
$R_1''$, $R_2''$ $R_3''$ represent hydrogen, chlorine, methyl, methoxy, ethoxy, nitro or cyano, $R_4'$ and $R_5'$ represent hydrogen, chlorine, bromine, benzoylamino, methoxy, ethoxy, methyl or acetylamino, $R_6'$ represents hydrogen, carbamoyl which is optionally substituted by $C_1$–$C_4$-alkyl, phenethyl, benzyl or phenyl, sulphamoyl which is optionally substituted by $C_1$–$C_4$-alkyl, phenethyl, benzyl or phenyl, cyano, nitro or $C_1$–$C_4$-alkoxy-carbonyl, $R_8'$ represents hydrogen, acetylamino or benzoylamino and $R'''$ represents hydrogen, $C_1$–$C_4$-alkyl, benzyl, phenethyl or phenyl which is optionally substituted by methyl, chlorine, methoxy, ethoxy, phenoxy which is optionally substituted by chlorine or methyl, carbamoyl, sulphamoyl, acetylamino, benzoylamino or nitro.

The dyestuffs of the formula I can be obtained by diazotising an amine of the formula $$D—NH_2 \quad\quad X$$

in which
D has the meaning given in the case of formula I, coupling the diazotisation product to a coupling component of the formula $$A—H \quad\quad XI$$

in which
A has the meaning given in the case of formula I, and working up the reaction mixture to give dyestuffs of the formula I.

The dyestuffs of the formula I, which have pigment properties, are obtained in a form suitable for pigments, or they can be converted into a suitable form by after-treatment processes which are known per se, for example by dissolving or swelling in strong inorganic acids, such as sulphuric acid, and discharging onto ice. Fine division can also be achieved by grinding with or without grinding auxiliaries, such as inorganic salts or sand, if appropriate in the presence of solvents, such as toluene, xylene, dichlorobenzene or N-methylpyrrolidone. The tinctorial strength and transparency of the pigment can be influenced by varying the after-treatment.

On the basis of their fastness to light and migration, the pigments of the formula I are suitable for the most diverse pigment applications. The pigments according to the invention can be used for the preparation of very fast pigmented systems, such as mixtures with other substances, formulations, paints, printing pastes, coloured paper and coloured macromolecular substances. By mixtures with other substances there may be understood, for example, those with inorganic white pigments, such as titanium dioxide (rutile), or with cement. Formulations are, for example, flush pastes with organic liquids or pastes and fine pastes with water, dispersing agents and, if appropriate, preservatives. The term paint means, for example, lacquers which dry physically or by oxidation, stoving lacquers, reactive lacquers, two-component lacquers, emulsion paints for weatherproof coatings and distempers. By printing pastes there are to be understood those for paper printing, textile printing and tin plate printing. The macromolecular substances can be of natural origin, such as rubber, or they can be obtained by chemical modification, such as acetylcellulose, cellulose butyrate or viscose, or synthetically produced, such as polymers, polyaddition products and polycondensates. Examples which may be mentioned are plastic compositions such as polyvinyl chloride, polyvinyl acetate, polyvinyl propionate, polyolefines, for example polyethylene or polypropylene, polyesters, for example polyethylene terephthalate, polyamides, high molecular weight polyamides, polymers and copolymers of acrylates, methacrylates, acrylonitrile, acrylamide, butadiene and styrene, and polyurethanes and polycarbonates. The substances pigmented with the claimed products can be in any desired form.

The pigments of the formula I according to the invention are furthermore outstandingly fast to water, oil, acid, lime, alkali, solvents, over-lacquering, over-spraying and sublimation and stable to heat and vulcanisation, and have a very high tinctorial strength and can readily be distributed in plastic compositions.

The coupling components of the formula XI are new and are prepared by processes which are known per se, for example as follows (the imides 3 formed can also be in the tautomeric form 3a):

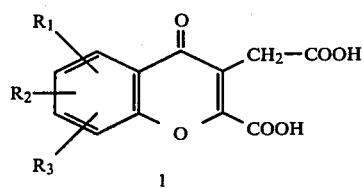 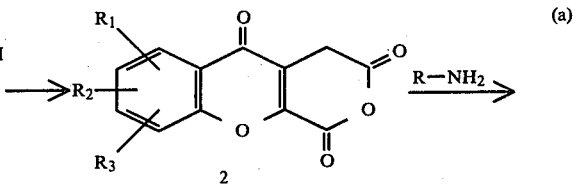

(a)

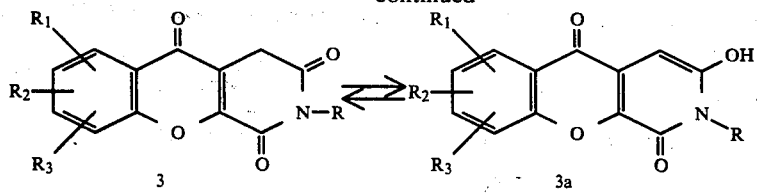

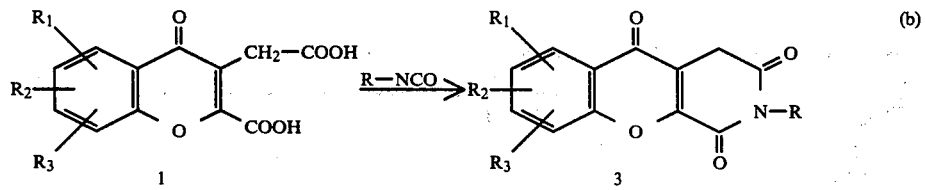

(b)

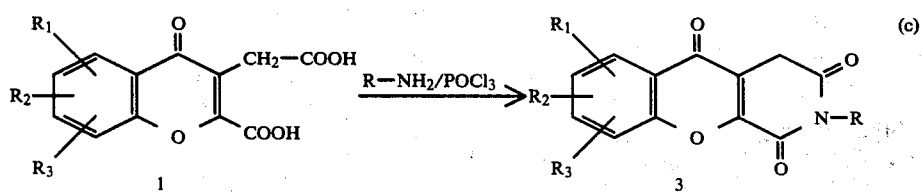

(c)

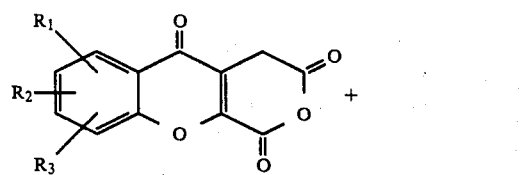

In the formulae 1, 2 and 3,
R, $R_1$, $R_2$ and $R_3$ have the meaning given in the case of formula I.

(d)

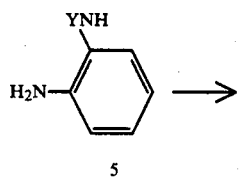

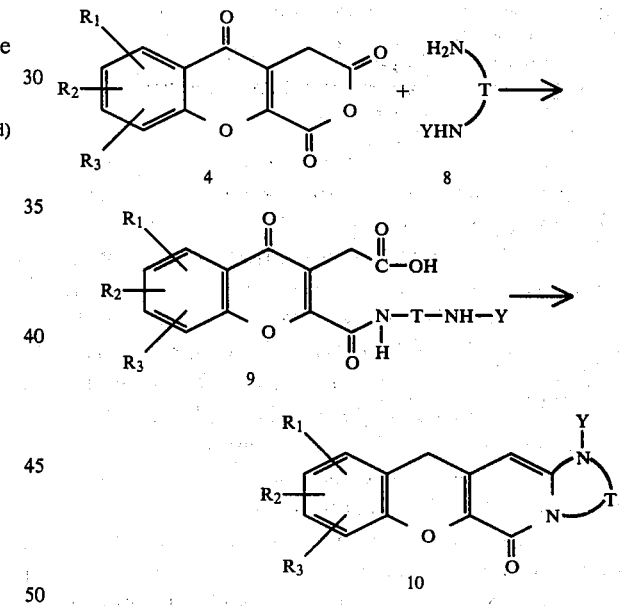

In the formulae 4, 5, 6 and 7,
$R_1$, $R_2$, $R_3$ and Y have the meaning given in the case of formula I.

The reaction can be represented generally by the following equation:

In the formulae 4, 8, 9 and 10,
$R_1$, $R_2$, $R_3$, T and Y have the abovementioned meaning.

The dicarboxylic acids of the formula 1 required as the starting material are known and/or they can be prepared by processes analogous to known processes (see, for example, German Offenlegungsschrift 2,731,566).

EXAMPLES

Example 1

15 g of 2-carboxy-3-carboxymethyl-chromone are introduced into 100 ml of acetyl chloride. The mixture is stirred at room temperature for 10 hours and then at the reflux temperature for 90 minutes; the initially strong evolution of HCl has then subsided. After cooling the mixture to 20° C., the anhydride of 2-carboxy-3- carboxymethylchromone which has formed is filtered off, rinsed with toluene and dried. Yield: 12 g (86.5%); melting point: 230°–232°; IR: 1760/1810 cm$^{-1}$.

Examples 2–7

The following anhydrides are obtained from the corresponding dicarboxylic acids in the same way as in Example 1:

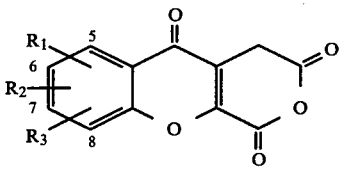

| Example No. | $R_1$ | $R_2$ | $R_3$ | Yield (%) | Melting point (°C.) |
|---|---|---|---|---|---|
| 2 | 6-Cl | 8-Cl | H | 65 | 214–216 |
| 3 | 6-Cl | H | H | 83 | 225–227 |
| 4 | 7-Cl | H | H | 74 | 216–218 |
| 5 | 6-Cl | 8-CH$_3$ | H | 76 | 243–245 |
| 6 | 6-CH$_3$ | H | H | 69 | 229–230 |
| 7 | 7-OCH$_3$ | H | H | 79 | 240 (decomposition) |

Example 8

23 g (0.1 mol) of the anhydride obtained according to Example 1 are added in portions to a solution of 18 g (0.11 mol) of 3,5-dichloroaniline in 100 of 1,3,5-trimethylbenzene and 60 ml of N-methylpyrrolidone in the course of 5 minutes and the mixture is stirred at 20° C. for 2 hours and then heated to the boiling point in the course of 30 minutes, a mixture of trimethylbenzene and water being distilled off. As soon as no further water is formed (after about 15 minutes), the mixture is allowed to cool, 100 ml of toluene are added and the product is filtered off. 24 g (64%) of N-(3,5-dichlorophenyl)-2-carboxy-3-carboxymethylchromone-imide are obtained; melting point: 258°–261° C.

The following compounds can also be obtained in accordance with the statements of Example 8:

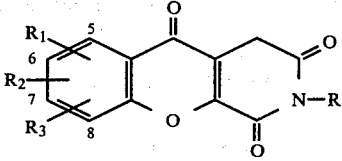

| Example No. | $R_1$ | $R_2$ | $R_3$ | R | Yield (%) | Melting point (°C.) |
|---|---|---|---|---|---|---|
| 9 | H | H | H | —⟨phenyl⟩—Cl | 65 | 225–226 |

-continued

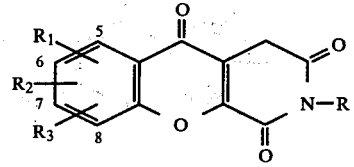

| Example No. | $R_1$ | $R_2$ | $R_3$ | R | Yield (%) | Melting point (°C.) |
|---|---|---|---|---|---|---|
| 10 | H | H | H | —⟨phenyl⟩ | 51 | 263–266 |
| 11 | H | H | H | —CH$_3$ | 54 | 271–274 |
| 12 | H | H | H | —H$_2$C—⟨phenyl⟩ | 64 | 263–265 |
| 13 | 6-Cl | H | H | —H$_2$C—⟨phenyl⟩ | 53 | 240–243 |
| 14 | 7-Cl | H | H | —H$_2$C—⟨phenyl⟩ | 49 | 216–218 |
| 15 | 6-Cl | 8-CH$_3$ | H | —H$_2$C—⟨phenyl⟩ | 52 | 248–250 |
| 16 | H | H | H | 6-Benzimideazobenzyl | 40 | 273–274 (decomposition) |
| 17 | 6-CH$_3$ | H | H | —H$_2$C—⟨phenyl⟩ | 38 | 191–194 |
| 18 | 6-Cl | 8-Cl | H | —H$_2$C—⟨phenyl⟩ | 43 | 295–298 |

Example 19

A solution of 25 g (0.1 mol) of p-(4-chlorophenoxy)-phenyl isocyanate in 25 ml of dichlorobenzene is added to a suspension of 24.8 g (0.1 mol) of 2-carboxy-3-carboxymethylchromone and 100 ml of 1,2-dichlorobenzene at 20°, the mixture is then warmed to 80° to 110°, whereupon strong evolution of CO$_2$ takes place, and after this has subsided, the mixture is heated to the boiling point (about 180°). The water formed is distilled off with dichlorobenzene (about 60 ml in 20 minutes), the mixture is allowed to cool and 100 ml of ether are added dropwise to the still hot solution (about 100°). After two hours, the product is filtered off. Yield: 33 g (77%) of N-p-(4'-chlorophenoxy)-phenyl-2-carboxy-3-carboxymethylchromone-imide; melting point: 223°–225°.

$C_{24}H_{14}ClNO_5$ (431.84): Calculated: C 66.75, H 3.27, N 3.24; Found: C 66.4, H 3.0, N 3.3.

The following compounds are prepared analogously to Example 19:

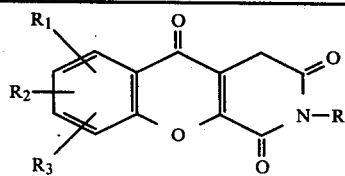

| Example No. | $R_1$ | $R_2$ | $R_3$ | R | Yield (%) | Melting point (°C.) |
|---|---|---|---|---|---|---|
| 20 | H | H | H | —⟨⟩—OC₂H₅ | 68 | 257–258 |
| 21 | H | H | H | —⟨⟩—NO₂ | 74 | 223–225 |
| 22 | H | H | H | —⟨⟩(Cl)(Cl) | 70 | 240–243 |
| 23 | 6-OCH₃ | H | H | —⟨⟩—O—⟨⟩—Cl | 72 | |

Example 24

4.2 g of o-phenylenediamine and 10 g of the compound

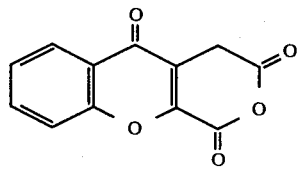

are stirred in 80 ml of tetrahydrofurane at 30°–35° C. for 12 hours. The solvent is distilled off and the residue is taken up in 40 ml of ethanol. The product of the formula

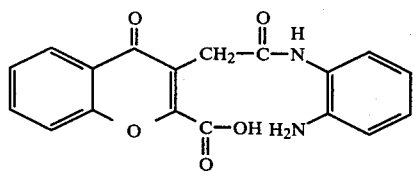

which has precipitated is filtered off. Yield: 7 g.

7 g of the compound thus obtained are boiled under reflux in 20 ml of N-methylpyrrolidone and 20 ml of trimethylbenzene for 30 minutes. The mixture is allowed to cool and the compound of the formula

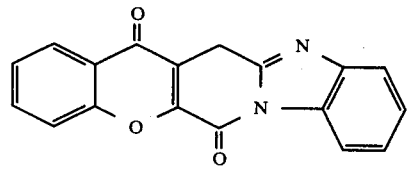

which has precipitated is filtered off.

Example 25

4.3 g of o-aminobenzylamine and 10 g of the compound

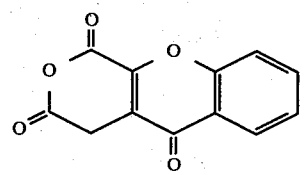

are stirred in tetrahydrofurane at 30°–35° C. for 12 hours. The solvent is distilled off and 40 ml of alcohol are added. The compound of the formula

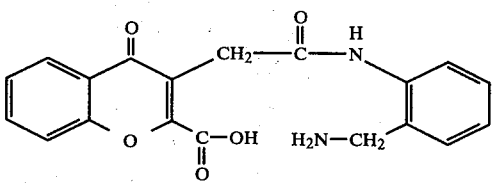

which has precipitated is filtered off, taken up in 25 ml of toluene and boiled under reflux for 12 hours. The water of reaction is thereby distilled off azeotropically. The mixture is allowed to cool and the product of the formula

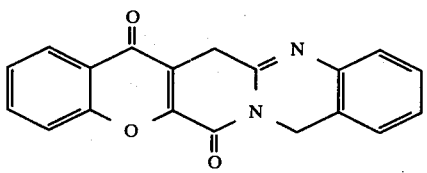

which has precipitated is filtered off.

Pigments of the formula I can be obtained as follows:

Example 26

2.5 g of 4-chloro-2-nitro-aniline are diazotised in 100 ml of glacial acetic acid and 30 ml of concentrated HCl with 10 ml of 10% strength NaNO$_2$ solution at 0° C. The mixture is subsequently stirred at 0° C. for 2 hours and is discharged onto 250 g of ice.

4.4 g of the compound of the formula

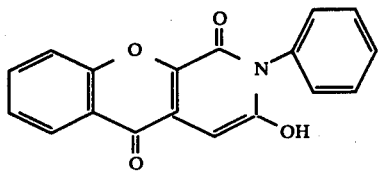

are dissolved in 30 ml of dimethylformamide and 30 ml of a 1% strength NaNO$_2$ solution and the solution is introduced into the diazonium salt solution described above. The pH value is adjusted to about 9 at 0° C. with 20% strength NaOH. The product which has precipitated is filtered off, dried and boiled up in nitrobenzene and then in dimethylformamide. A reddish-tinged yellow pigment of the formula

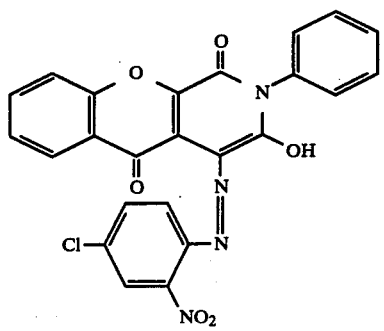

with good properties in use is obtained.

Further pigments are obtained if the diazo components listed in the table below are reacted in the same manner as in Example 26 with the coupling components listed.

| Example No. | Diazo component | Coupling component | Colour shade |
|---|---|---|---|
| 27 | 4-chloro-2-cyano-aniline | (N-CH$_3$ coupling component) | strong greenish-tinged yellow |
| 28 | 4-chloro-2-nitro-aniline | " | reddish-tinged yellow |
| 29 | 4-methoxy-2-nitro-aniline | " | orange |
| 30 | 1-aminoanthraquinone | " | orange |
| 31 | 1-amino-5-benzoylamino-anthraquinone | " | reddish-tinged orange |

-continued

| Example No. | Diazo component | Coupling component | Colour shade |
|---|---|---|---|
| 32 | 3-amino-4-chlorobenzamide (Cl, NH₂, C(=O)NH₂ on benzene) | " | reddish-tinged yellow |
| 33 | 4-amino-3-chlorobenzamide (H₂N-C(=O)-, Cl, NH₂ on benzene) | " | reddish-tinged yellow |
| 34 | 5-amino-2,3-dihydro-1H-benzimidazol-2-one | " | yellow |
| 35 | " | 3-benzoyl-1-phenyl-6-hydroxy-2-oxo-1,2-dihydropyridine-chromone type structure (benzoyl-substituted 1-phenyl-6-hydroxy-2(1H)-pyridinone) | yellow |
| 36 | 2-chloro-4-nitroaniline | " | reddish-tinged yellow |
| 37 | 4,5-dichloro-2-nitroaniline (NO₂, NH₂, Cl, Cl on benzene) | " | reddish-tinged yellow |
| 38 | 5-chloro-2-ethoxy-4-amino-... (C₂H₅O, Cl, NH₂, NO₂ on benzene) | " | orange |
| 39 | 1-amino-5-acetylaminoanthraquinone (H₃C-C(=O)-NH on anthraquinone with NH₂) | " | orange |

-continued

| Example No. | Diazo component | Coupling component | Colour shade |
|---|---|---|---|
| 40 | 1-amino-5-(phenylaminocarbonylamino)anthraquinone | " | reddish-tinged orange |
| 41 | 2,3,5-trichloroaniline | " | greenish-tinged yellow |
| 42 | 2-chloro-4-amino-5-methoxy-benzanilide | " | yellow |
| 43 | 3-bromo-4-amino-benzamide | " | reddish-tinged yellow |
| 44 | 4-chloro-2-nitroaniline | " | reddish-tinged yellow |
| 45 | 2,5-dichloro-4-amino-acetanilide | " | reddish-tinged yellow |
| 46 | 2-amino-4-chloro-benzonitrile | 1-benzyl-3-(2-hydroxy-4-oxo-4H-chromen-3-carbonyl)-6-hydroxy-2-pyridone | greenish-tinged yellow |
| 47 | 2-amino-1,4-dicyanobenzene | " | reddish-tinged yellow |

-continued
| Example No. | Diazo component | Coupling component | Colour shade |
|---|---|---|---|
| 48 | 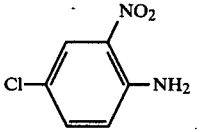 | " | reddish-tinged yellow |
| 49 | 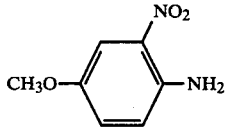 | " | reddish-tinged yellow |
| 50 | 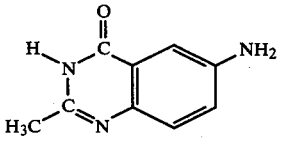 | " | yellow |
| 51 | 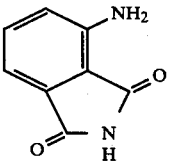 | " | yellow |
| 52 | 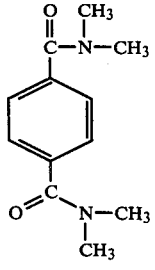 | " | reddish-tinged yellow |
| 53 | 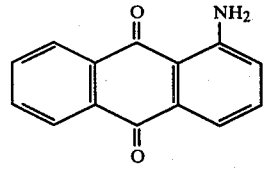 | " | orange |
| 54 | 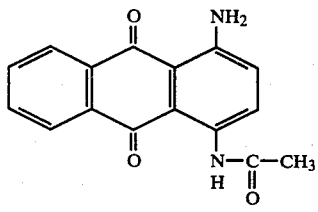 | " | brown |
| 55 | 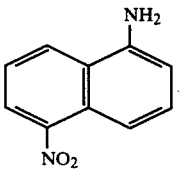 | " | orange |

-continued

| Example No. | Diazo component | Coupling component | Colour shade |
|---|---|---|---|
| 56 | 4-amino-2,5-dichloro-benzenesulfonamide (Cl, NH2, H2NO2S, Cl) | " | orange |
| 57 | 4-chloro-2-nitroaniline | 3-(4-chloro-2-hydroxybenzoyl)-1-phenyl-pyridine-2,6-dione derivative | orange |
| 58 | " | 3-(4-chloro-2-hydroxy-6-methylbenzoyl)-1-phenyl-pyridine-2,6-dione derivative | orange |
| 59 | " | 3-(4,6-dichloro-2-hydroxybenzoyl)-1-phenyl-pyridine-2,6-dione derivative | orange |
| 60 | 1-aminoanthraquinone | " | orange |
| 61 | " | 3-(2-chloro-4-methoxy-6-hydroxybenzoyl)-1-butyl-pyridine-2,6-dione derivative | orange |
| 62 | " | 3-(4-bromo-2-hydroxy-6-methylbenzoyl)-1-(4-methoxyphenyl)-pyridine-2,6-dione derivative | orange |
| 63 | " | 3-(4-phenoxybenzoyl)-1-(4-propoxybutyl)-pyridine-2,6-dione derivative | orange |

-continued

| Example No. | Diazo component | Coupling component | Colour shade |
|---|---|---|---|
| 64 | 4-chloro-2-nitroaniline | " | orange |
| 65 | " | (structure shown: chromone-type coupler with N-(4-(4-chlorophenoxy)phenyl) group) | orange |
| 66 | 4-methoxy-2-nitroaniline | " | scarlet |
| 67 | 5-chloro-2-nitroaniline | " | orange |
| 68 | 1-aminoanthraquinone | " | orange |
| 69 | 1-amino-5-benzoylamino-anthraquinone | " | scarlet |
| 70 | N-(2,4-dichlorobenzoyl)-2,5-dimethoxy-1,4-phenylenediamine | " | reddish-tinged yellow |
| 71 | N-(2,5-dichlorobenzoyl)-2,5-dichloro-1,4-phenylenediamine | " | reddish-tinged yellow |

| Example No. | Diazo component | Coupling component | Colour shade |
|---|---|---|---|
| 72 | 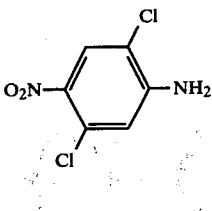 | 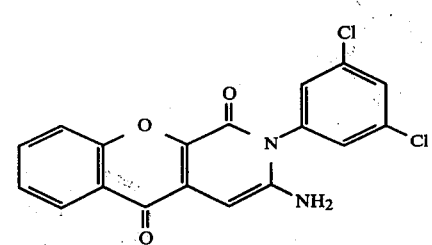 | orange |
| 73 | 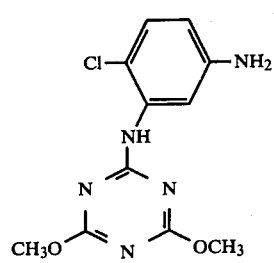 | " | yellow |
| 74 | 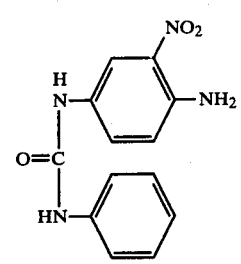 | " | yellow-brown |
| 75 | 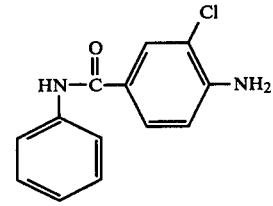 | 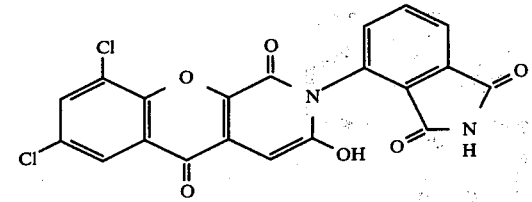 | yellow |
| 76 | 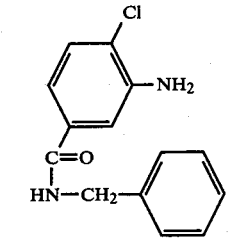 | 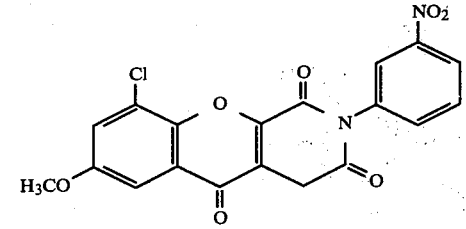 | yellow |
| 77 | 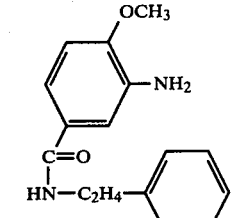 | " | yellow |

-continued
| Example No. | Diazo component | Coupling component | Colour shade |
|---|---|---|---|
| 78 | 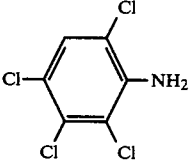 | 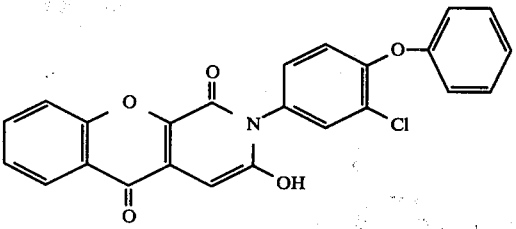 | reddish-tinged yellow |
| 79 | 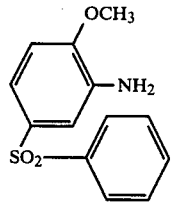 | 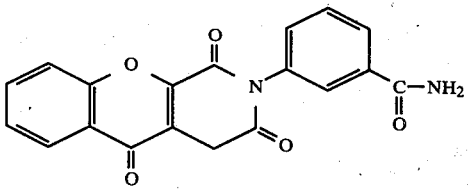 | reddish-tinged yellow |
| 80 | 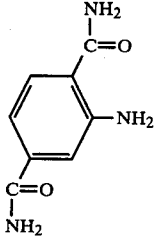 | 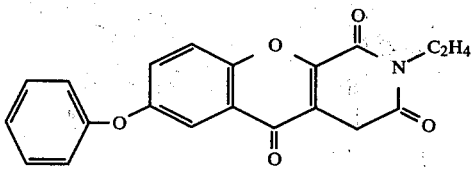 | reddish-tinged yellow |
| 81 | 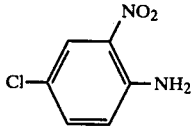 | 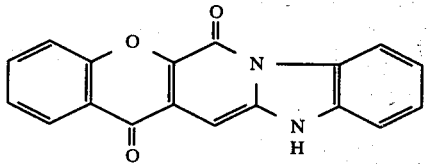 | red |
| 82 | 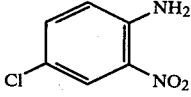 | 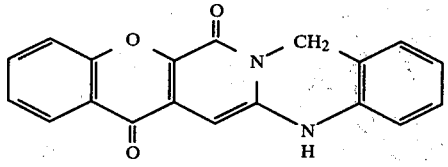 | red |
| 83 | 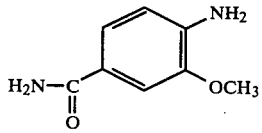 | " | red |
| 84 | 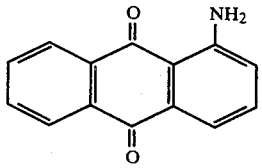 | " | red |

-continued

| Example No. | Diazo component | Coupling component | Colour shade |
|---|---|---|---|
| 85 | " | [structure with Cl, O, NH] | red |
| 86 | 4-C₂H₅O, 2-NO₂ aniline | [structure with Cl, Cl, CH₃, Cl, NH] | red |
| 87 | C₆H₅-NH-C(=O)-C₆H₄-SO₂-N(C₂H₅)(C₂H₃) | [structure with O-C₆H₄-Cl, NH] | red |
| 88 | 2,5-dichloro-N-(2,5-dichloro-4-aminophenyl)benzamide | [structure with NH] | red |
| 89 | 3-amino-4-nitro-N-phenyl benzamide | [structure with Cl, Cl, CH₃, NH] | red-brown |
| 90 | 2-chloro-5-methoxy aniline | [structure with Cl, Cl, NO₂, NH] | yellowish-tinged red |

-continued
| Example No. | Diazo component | Coupling component | Colour shade |
|---|---|---|---|
| 91 | 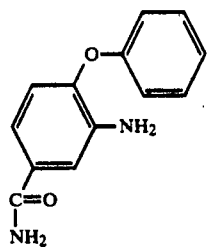 | 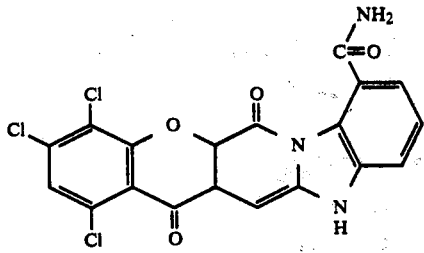 | |
| 92 | 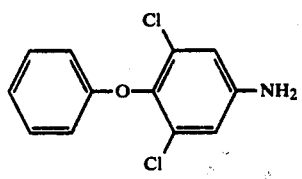 | 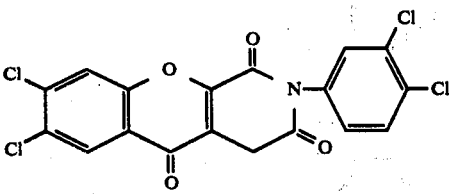 | yellow |
| 93 | 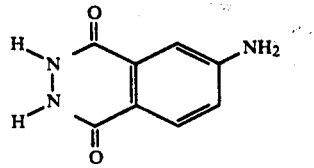 | 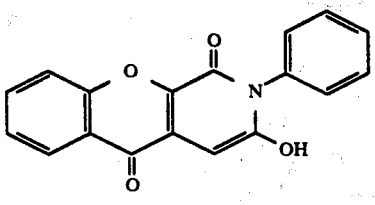 | reddish-tinged yellow |
| 94 | 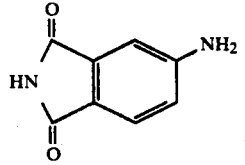 | 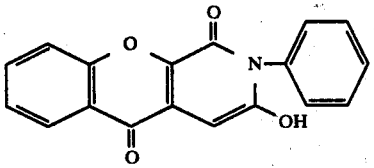 | reddish-tinged yellow |
| 95 | 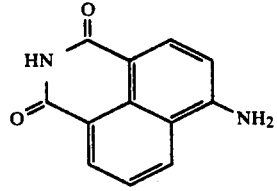 | " | scarlet |
| 96 | 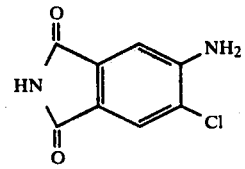 | " | scarlet |
| 97 | 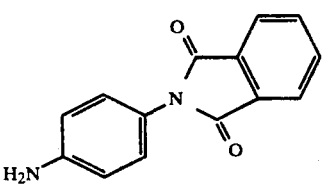 | " | yellow |

-continued

| Example No. | Diazo component | Coupling component | Colour shade |
|---|---|---|---|
| 98 | [structure: 3-bromo-4-amino-phenyl-NH-C(=N-)-N(-C(OCH3)=N-)-OCH3 guanidine derivative] | " | yellow |
| 99 | [structure: 2-amino-4-ethoxy-benzonitrile] | " | greenish-tinged yellow |
| 100 | [structure: 2-nitro-4-chloro-aniline] | [structure: chromone-pyridone coupler with phthalimide-phenyl group] | reddish-tinged yellow |
| 101 | [structure: 2-nitro-4-methoxy-aniline] | " | scarlet |
| 102 | [structure: 2-amino-4-chloro-benzonitrile] | " | greenish-tinged yellow |
| 103 | [structure: 2-nitro-4-phenoxy-aniline] | " | scarlet |
| 104 | [structure: 4-chloro-1,3-diaminobenzene] | [structure: chromone-pyridone coupler with benzimidazolone group] | reddish-tinged yellow |
| 105 | [structure: 1-aminoanthraquinone] | " | orange |

-continued
| Example No. | Diazo component | Coupling component | Colour shade |
|---|---|---|---|
| 106 | 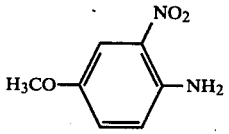 | " | scarlet |
| 107 | 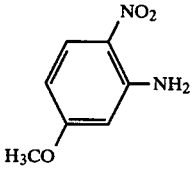 | " | orange |
| 108 | 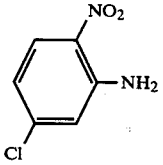 | 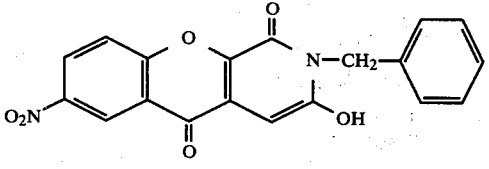 | reddish-tinged yellow |
| 109 | 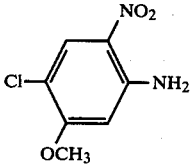 | 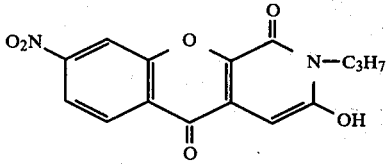 | orange |
| 110 | 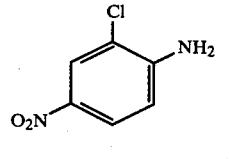 | 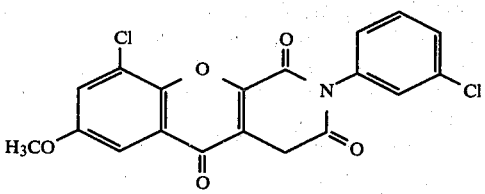 | reddish-tinged yellow |
| 111 | 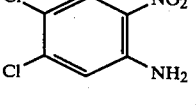 | 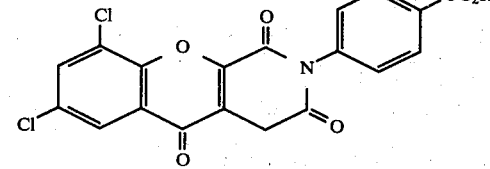 | orange |
| 112 | 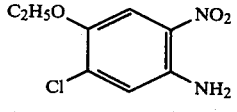 | 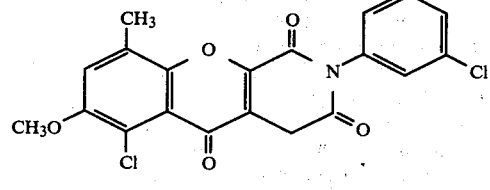 | scarlet |
| 113 | 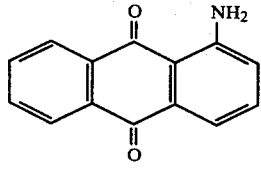 | 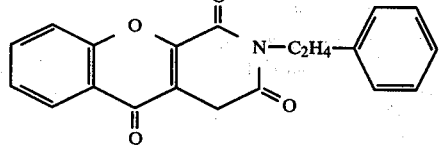 | reddish-tinged orange |

| Example No. | Diazo component | Coupling component | Colour shade |
|---|---|---|---|
| 114 | 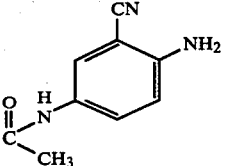 | 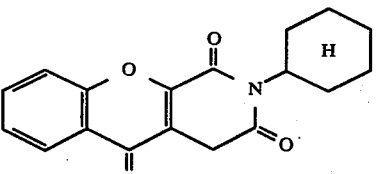 | reddish-tinged yellow |
| 115 | " | 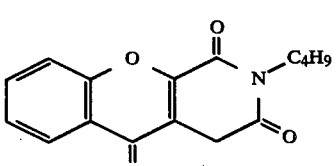 | reddish-tinged yellow |
| 116 | 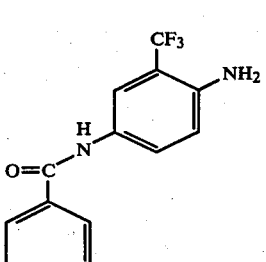 | 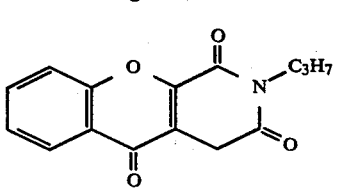 | reddish-tinged yellow |

Example 117

(a) 8 g of the finely divided pigment obtained according to Example 26 are ground on an automatic Hoover-Muller grinder with a stoving lacquer consisting of 25 g of coconut oil alkyd resin (40% of coconut oil), 10 g of melamine resin, 50 g of toluene and 7 g of glycol monomethyl ether. The mixture is applied to the substrate to be lacquered and the lacquer is hardened by stoving at 130° C. to give reddish-tinged yellow lacquerings with very good fastness to over-lacquering and outstanding fastness to light and weathering.

Pigmented stoving lacquers with the same fastness properties are obtained if 15-25 g of the alkyd resin indicated or of an alkyd resin based on cottonseed oil, dehydrated castor oil, castor oil or synthetic fatty acids are used, and 10-15 g of the melamine resin mentioned or of a condensation product of formaldehyde with urea or with benzoguanamine are used instead of the amount of melamine resin indicated.

(b) If 1 to 10 g of a mixture of titanium dioxide (rutile type) with the pigment indicated in Example 26 in the ratio 0.5-50:1 are ground into the lacquer described in Example 117a instead of the amount of pigment indicated, the same further processing gives lacquerings with the same fastness properties and with a reddish-tinged yellow colour shade which shifts towards white with an increasing content of titanium dioxide.

Example 118

6 g of finely divided pigment according to Example 30 are ground into 100 g of nitrocellulose lacquer consisting of 44 g of collodion cotton (low-viscosity, 35% strength, butanol-moist), 5 g of dibutyl phthalate, 40 g of ethyl acetate, 20 g of toluene, 4 g of n-butanol and 10 g of glycol monomethyl ether. After brushing the lacquer onto a substrate and drying, reddish-tinged yellow lacquerings of outstanding fastness to light and over-lacquering are obtained. The same results are obtained using nitrocellulose lacquers which have a nitrocellulose content of 10-15 g and a plasticiser content of 5-10 g and contain 70-80 g of a solvent mixture, aliphatic esters, such as ethyl acetate and butyl acetate, and aromatics, such as toluene and xylene, and relatively small proportions of aliphatic ethers, such as glycol ether, and alcohols, such as butanol, preferably being used. By plasticisers there may be understood, for example: phthalates, such as dioctyl phthalate and dibutyl phthalate, esters of phosphoric acid, and castor oil, alone or in combination with oil-modified alkyd resins.

Lacquerings with similar fastness properties are obtained using other spirit lacquers, Zapon lacquers and nitrocellulose lacquers which dry physically, air-drying oil varnishes, synthetic resin lacquers and nitrocellulose combination lacquers, and oven-drying and air-drying epoxide resin lacquers, if appropriate in combination with urea resins, melamine resins, alkyd resins or phenolic resins.

EXAMPLE 119

5 g of finely divided pigment according to Example 30 are ground in a porcelain ball mill with 100 g of an unsaturated polyester resin which dries without paraffin. 10 g of styrene, 59 g of melamine/formaldehyde resin and 1 g of a paste consisting of 40% of cyclohexanone peroxide and 60% of dibutyl phthalate are stirred thoroughly with the ground material, and finally 4 g of dryer solution (10% strength cobalt naphthenate in white spirit) and 1 g of silicone oil solution (1% strength in xylene) are admixed. The mixture is applied to primed wood and a high-gloss, water-resistant orange-red lacquering which is fast to weathering and has outstanding fastness to light is obtained.

If amine-hardening epoxide resin lacquers with dipropylenediamine as the amine component are used instead of the reactive lacquer based on unsaturated polyester resins, orange-red lacquerings of outstanding fastness to weathering and effluorescence are obtained.

EXAMPLE 120

100 g of a 65% strength solution of an aliphatic polyester, with about 8% of free hydroxyl groups, in glycol monoethyl ether-acetate are ground with 5 g of the pigment obtained according to Example 26 and the ground material is then mixed thoroughly with 44 g of a 67% strength solution of the reaction product of 1 mol of trimethylolpropane and 3 mols of toluylene diisocyanate. Without impairment of the pot life, after application of the mixture and reaction of the components, high-gloss reddish-tinged yellow polyurethane lacquerings of outstanding fastness to effluorescence, light and weathering result.

Pigmentation of similar fastness is obtained using other two-component lacquers based on aromatic or aliphatic isocyanates and polyethers or polyesters containing hydroxyl groups, and with polyisocyanate lacquers which dry in the presence of moisture and give polyurea lacquerings.

EXAMPLE 121

5 g of a fine paste obtained by kneading 50 g of the pigment obtained according to Example 30 with 15 g of an aryl polyglycol ether emulsifier and 35 g of water are mixed with 10 g of baryte, as the filler, 10 g of titanium dioxide (rutile type) as a white pigment, and 40 g of an aqueous emulsion paint containing about 50% of polyvinyl acetate. The paint is brushed onto the substrate and, after drying, orange paint films of very good fastness to lime and cement and outstanding fastness to weathering and light are obtained.

The fine paste obtained by kneading is likewise suitable for pigmenting clear polyvinyl acetate emulsion paints, and for emulsion paints which contain copolymers of styrene and maleic acids as binders and emulsion paints based on polyvinyl propionate, polymethacrylate or butadiene/styrene.

EXAMPLE 122

10 g of the pigment paste mentioned in Example 121 are mixed with a mixture of 5 g of chalk and 5 g of 50% strength size solution. A reddish-tinged yellow wallpaper paint with which coatings of outstanding fastness to light are achieved is obtained. To prepare the pigment paste, it is also possible to use other non-ionic emulsifiers, such as the reaction products of nonylphenol and ethylene oxide, or ionic wetting agents, such as the sodium salts of alkylarylsulphonic acids, for example of dinaphthylmethanedisulphonic acid, sodium salts of substituted sulpho-fatty acid esters and sodium salts of paraffinsulphonic acids, in combination with alkyl polyglycol ethers.

EXAMPLE 123

A mixture of 65 g of polyvinyl chloride, 35 g of diisooctyl phthalate, 2 g of dibutyl-tin mercaptide, 0.5 g of titanium dioxide and 0.5 g of the pigment of Example 31 is compounded on a mixing mill at 165° C. An intensely reddish-tinged orange mass which can be used for producing films or shaped articles is obtained. The coloration is distinguished by outstanding fastness to light and very good fastness to plasticisers.

EXAMPLE 124

0.2 g of the pigment according to Example 26 is mixed with 100 g of polyethylene granules, polypropylene granules or polystyrene granules. The mixture can be either injection-moulded directly in an injection-moulding machine at 220° to 280° C., or processed to coloured rods in an extruder or to coloured hides on a mixing mill. If appropriate, the rods and hides are granulated and the granules injection-moulded in an injection-moulding machine.

The reddish-tinged yellow moulded articles have very good fastness to light and migration. Synthetic polyamides of caprolactam or adipic acid and hexamethylenediamine, or the condensation products of terephthalic acid and ethylglycol can be coloured in a similar manner at 280° to 300° C., if appropriate under a nitrogen atmosphere.

EXAMPLE 125

1 g of the pigment according to Example 40, 10 g of titanium dioxide (rutile type) and 100 g of a pulverulent copolymer based on acrylonitrile/butadiene/styrene are mixed and the mixture is compounded on a roll mill at 140°–180° C. A reddish-tinged yellow hide is obtained and is granulated and the granules are injection-moulded in an injection-moulding machine at 200°–250° C. Orange-coloured moulded articles of very good fastness to light and migration and excellent stability to heat are obtained.

Plastics based on cellulose acetate, cellulose butyrate and mixtures thereof can be coloured in shades with similar fastness properties in a similar manner, but at temperatures of 180°–220° C. and without the addition of titanium dioxide.

EXAMPLE 126

0.2 g of finely divided pigment according to Example 26 is mixed with 100 g of a plastic based on polycarbonate in an extruder or in a kneading screw at 250°–280° C. and the mixture is processed to granules. Reddish-tinged yellow, transparent granules of outstanding fastness to light and stability to heat are obtained.

EXAMPLE 127

90 g of a slightly branched polypropylene glycol with a molecular weight of 2,500 and a hydroxyl number of 56, 0.25 g of endoethylenepiperazine, 0.3 g of tin-II octoate, 1.0 g of a polyether siloxane, 3.5 g of water and 12.0 g of a paste of 10 g of the pigment according to Example 26 in 50 g of the polypropylene glycol indicated are mixed thoroughly with one another, the mixture is then mixed intimately with 45 g of toluylene diisocyanate (80% of the 2,4-isomer and 20% of the 2,6-isomer), and the final mixture is poured into a mould. After 6 seconds, the mixture becomes cloudy and foams. After 70 seconds, an intensively reddish-tinged yellow soft polyurethane foam has formed, the pigmentation of which has outstanding fastness to light.

EXAMPLE 128

90 g of a slightly branched polyester of adipic acid, diethylene glycol and trimethylolpropane which has a molecular weight of 2,000 and a hydroxyl number of 60 are mixed with the following components: 1.2 g of dimethylbenzylamine, 2.5 g of sodium castor oil-sulphate, 2.0 g of an oxyethylated, benzylated hydroxydiphenyl, 1.75 g of water and 12 g of a paste prepared by grinding 10 g of the pigment according to Example 26 in 50 g of the above-mentioned polyester. After the mixing, 40 g of toluylene diisocyanate (65% of the 2,4-isomer and 35% of the 2,6-isomer) are stirred in and the mixture is poured into a mould and foamed. After 60 seconds, a reddish-tinged yellow, soft polyurethane foam has formed, the coloration of which is distinguished by very good fastness to light.

EXAMPLE 129

Deep reddish-tinged yellow offset prints of high brilliancy and very good fastness of light and lacquering are obtained with a printing paste prepared by grinding 35 g of the pigment according to Example 26 with 65 g of linseed oil and adding 1 g of siccative (Co naphthenate, 50% strength in white spirit). Using this printing paste in letterpress printing, collotype printing, lithographic printing or die stamping leads to reddish-tinged yellow prints with similar fastness properties. If the pigment is used for colouring tinplate printing pastes or low-viscosity gravure printing pastes or printing inks, reddish-tinged yellow prints with similar fastness properties are obtained.

EXAMPLE 130

A printing paste is prepared from 10 g of the fine pigment paste indicated in Example 121, 100 g of 3% strength tragacanth gum, 100 g of an aqueous 50% strength egg albumin solution and 25 g of a non-ionic wetting agent. A textile fibre fabric is printed with this paste and steamed at 100° C. and a reddish-tinged yellow print which is distinguished by excellent fastness properties, in particular fastness to light, is obtained. Other binders which can be used for fixing the pigment onto the fibre, for example binders based on synthetic resin, or British gum or cellulose glycolate, can be used in the printing formulation instead of the tragacanth gum and egg albumin.

EXAMPLE 131

A mixture of 100 g of light crepe, 2.6 g of sulphur, 1 g of stearic acid, 1 g of mercaptobenzthiazole, 0.2 g of hexamethylenetetramine, 5 g of zinc oxide, 60 g of chalk and 2 g of titanium dioxide (anatase type) is compounded on a mixing mill at 50° C. and coloured with 2 g of the pigment obtained according to Example 26, and the final mixture is then vulcanised at 140° C. for 12 minutes. A reddish-tinged yellow vulcanisation product of very good fastness to light is obtained.

EXAMPLE 132

22.5 l of an aqueous, approximately 9% strength viscose solution are added, in a stirred apparatus, to 100 g of a 20% strength aqueous paste of the pigment according to Example 26, which has been prepared, for example, by dissolving the pigment in 96% strength sulphuric acid, discharging the solution onto ice, filtering the mixture and washing the material on the filter with water until neutral. The coloured composition is stirred for 15 minutes and then deaerated and subjected to a spinning and desulphurising process.

Reddish-tinged yellow filaments or films with very good fastness to light are obtained.

EXAMPLE 133

10 kg of paper pulp containing 4 g of cellulose per 100 g are treated in a hollander for about 2 hours. During this period, 4 g of rosin size, then 30 g of an approximately 15% strength pigment dispersion obtained by grinding 4.8 g of the pigment obtained according to Example 26 with 4.8 g of dinaphthylmethanedisulphonic acid and 22 g of water in a ball mill, and then 5 g of aluminium sulphate are added, in each case at intervals of a quarter of an hour.

After finishing on a paper-making machine, reddish-tinged yellow paper of outstanding fastness to light is obtained.

EXAMPLE 134

The reddish-tinged yellow-pigmented paper produced according to Example 133 is impregnated with a 55% strength solution of a urea/formaldehyde resin in n-butanol and baked at 140° C. Reddish-tinged yellow laminated paper of very good fastness to migration and outstanding fastness to light is obtained.

Laminated paper with the same fastness properties is obtained by laminating paper which has been printed, by the gravure printing process, with a printing paste containing the fine orange-coloured pigment paste described in Example 121 and water-soluble or saponifiable binders.

We claim:

1. Dyestuffs of the formula

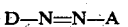 I in which

D represents the radical of a diazo component and
A represents the radical of a coupling component of the formula

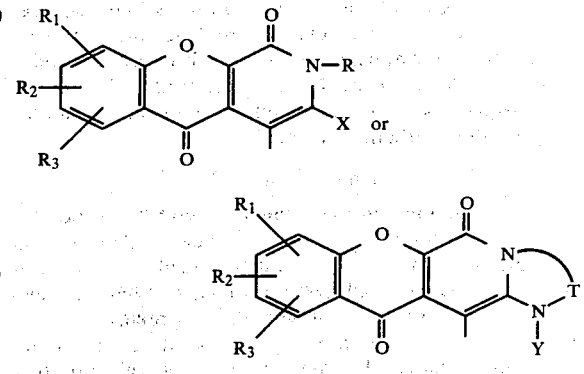

wherein

R₁, R₂ and R₃ represent hydrogen or non-ionic radicals,
R represents hydrogen or an optionally substituted alkyl, cycloalkyl, aryl, aralkyl or heterocyclic radical,
X represents OH or

T represents the remaining members of a fused-on ring and

Y and Z represent hydrogen, optionally substituted alkyl or optionally substituted aryl.

2. Dyestuffs according to claim 1, in which

D represents the radical of a diazo component of the benzene, naphthalene, anthraquinone or heterocyclic series, it being possible for the phenyl, naphthyl, anthraquinonyl or heterocyclic radicals of the diazo component to be substituted by nitro, cyano, halogen, preferably chlorine or bromine, carbamoyl or sulphamoyl, it being possible for the carbamoyl and sulphamoyl radicals to be monosubstituted or disubstituted by $C_1$-$C_4$-alkyl, benzyl, phenethyl or phenyl, which in its turn can be further substituted by chlorine, bromine, $C_1$-$C_4$-alkyl and $C_1$-$C_4$-alkoxy, alkylsulphonyl, preferably arylsulphonyl, preferably phenyl- or naphthylsulphonyl, alkoxy, aryloxy, alkyl, alkoxycarbonyl, trifluoromethyl, acylamino, benzoylamino which is optionally substituted by chlorine, methyl, methoxy or ethoxy, phenylacetylamino, $C_1$-$C_4$-alkylaminocarbonylamino, phenylaminocarbonylamino, phenoxycarbonylamino or s-triazinylamino, it being possible for the s-triazinyl radical to be substituted by Cl, Br, F or $C_1$-$C_4$-alkoxy, $R_1$, $R_2$ and $R_3$ represent hydrogen, alkyl, preferably $C_1$-$C_4$-alkyl, halogen, preferably chlorine or bromine, alkoxy, carbamoyl, sulphamoyl, aryloxy, alkoxycarbonyl, alkylsulphonyl, arylsulphonyl, aryl, acylamino, benzoylamino which is optionally substituted by chlorine, methyl, methoxy or ethoxy, phenylacetylamino, $C_1$-$C_4$-alkylaminocarbonylamino, phenylaminocarbonylamino, phenoxycarbonylamino, nitro or cyano;

R represents hydrogen, $C_1$-$C_8$-alkyl which is optionally substituted by $C_1$-$C_4$-alkoxy, (mono- or di-$C_1$-$C_4$-alkyl)-amino, carbamoyl, sulphamoyl, acylamino, phenylacetylamino, ($C_1$-$C_4$-alkyl)-carbonylamino, phenylaminocarbonylamino or phenoxycarbonylamino, it being possible for benzoylamino in its turn to be further substituted by chlorine, methyl, methoxy or ethoxy; or phenyl or naphthyl which is optionally substituted by $C_1$-$C_4$-alkyl, $C_1$-$C_4$-alkoxy, phenoxy, halogen, carbamoyl or acylamino; or a cyclopentyl or cyclohexyl radical which is optionally substituted by phenyl, which can be substituted by halogen, $C_1$-$C_4$-alkyl or $C_1$-$C_4$-alkoxy, or by $C_1$-$C_4$-alkoxy, carbamoyl, benzoylamino which is optionally substituted by chlorine, methyl, methoxy or ethoxy, phenylacetylamino, ($C_1$-$C_4$-alkyl)carbonylamino, phenylaminocarbonylamino or phenoxycarbonylamino; or benzyl or phenethyl which is optionally substituted by halogen, $C_1$-$C_4$-alkyl or $C_1$-$C_4$-alkoxy in the phenyl radical; or represents a radical

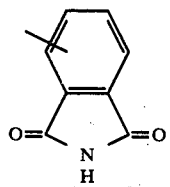

T designates the remaining members which are necessary to form a 5-membered or 6-membered saturated or unsaturated ring which includes the two N atoms already present; and Y and Z represent hydrogen, an optionally substituted $C_1$-$C_8$-alkyl radical, an optionally substituted phenyl radical or an optionally substituted naphthyl radical, the substituents of these radicals corresponding to those above for R in the meaning of optionally substituted $C_1$-$C_8$-alkyl, optionally substituted phenyl or optionally substituted naphthyl.

3. Dyestuff of the formula

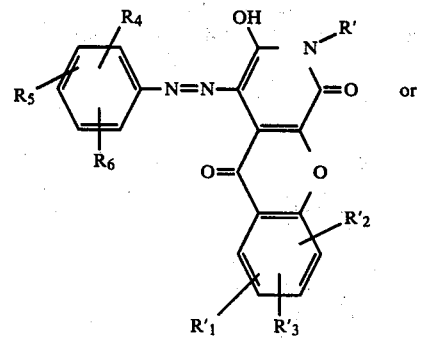

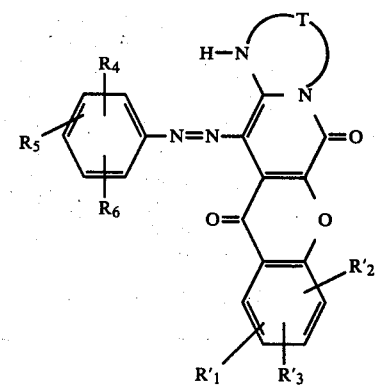

wherein

T has the meaning given in claim 1

R' represents hydrogen, $C_1$-$C_8$-alkyl which can be substituted by Cl, Br, $C_1$-$C_4$-alkoxy or (mono-$C_1$-$C_4$- or di-$C_1$-$C_4$-alkyl)-amino, phenyl which can be substituted by Cl, Br, $C_1$-$C_4$-alkyl, $C_1$-$C_4$-alkoxy, phenoxy which is optionally substituted by Cl, Br, methyl or nitro, nitro, carbamoyl, sulphamoyl, benzoylamino, acetylamino or phthaloylamino, benzyl or phenethyl which can be substituted in the phenyl radical by Cl, Br, methoxy, ethoxy, methyl or nitro, cyclohexyl or a radical

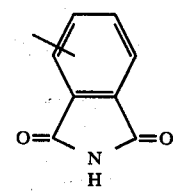

$R_1'$ and $R_2'$ represent hydrogen, methyl, chlorine, bromine, methoxy, ethoxy or phenoxy, $R_3'$ represents hydrogen, acetylamino, benzoylamino or methyl and R4, R5 and R6 represent hydrogen, chlorine, bromine, methyl, methoxy, ethoxy, phenoxy, trifluoromethyl, nitro, $C_1$–$C_4$-alkyl, cyano, acetylamino, benzoylamino which is optionally substituted by Cl, or sulphamoyl or carbamoyl, it being possible for the sulphamoyl and carbamoyl radicals also to be monosubstituted or disubstituted by phenyl, which can in its turn be further substituted by chlorine, methoxy, ethoxy or methyl, or by benzyl, phenethyl and/or $C_1$–$C_4$-alkyl, or $C_1$–$C_4$-alkylsulphonyl, phenylsulphonyl, phenylaminocarbonyl and/or phenylaminocarbonylamino.

4. A dyestuff according to claim 3 of the formula

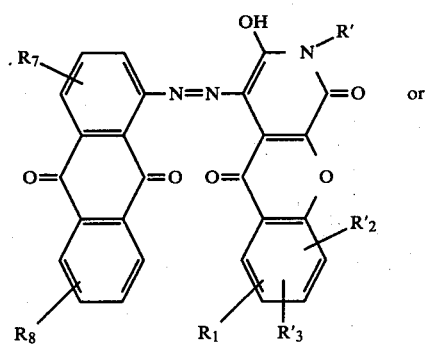

IV or

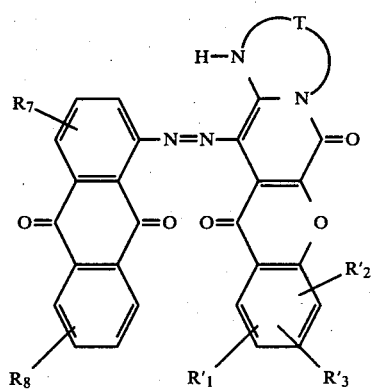

V in which
R7 and R8 represent hydrogen, $C_1$–$C_4$-alkyl, chlorine, bromine, benzoylaminocarbonylamino, ($C_1$–$C_4$-alkyl)-carbonylamino, ($C_1$–$C_4$-alkyl)aminocarbonylamino, phenylaminocarbonylamino, benzoylamino which is optionally substituted by chlorine, bromine, $C_1$–$C_4$-alkyl or $C_1$–$C_4$-alkoxy, or phenylsulphonylamino.

5. A dyestuff according to claim 3 of the formula

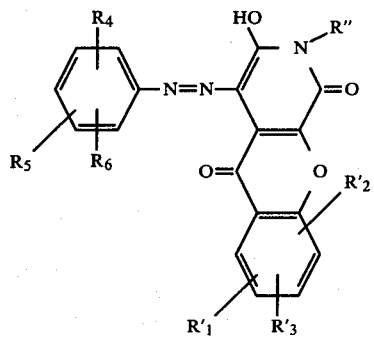

VI

-continued
or

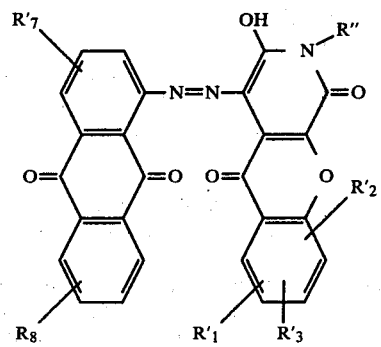

VII in which
R8 represents hydrogen, $C_1$–$C_4$-alkyl, chlorine, bromine, benzoylaminocarbonylamino, ($C_1$–$C_4$-alkyl) carbonylamino, ($C_1$–$C_4$-alkyl), aminocarbonylamino, phenylaminocarbonylamino, benzoylamino which is optionally substituted by chlorine, bromine, $C_1$–$C_4$-alkyl or $C_1$–$C_4$-alkoxy or phenylsulphonylamino, R'' represents hydrogen, $C_1$–$C_4$-alkyl, phenyl, benzyl or phenethyl, it being possible for the phenyl radicals in phenyl, benzyl and phenethyl to be substituted by chlorine, bromine, methoxy, ethoxy, phenoxy, aminocarbonyl, acetylamino or benzoylamino, or phthalylamino or a radical of the formula

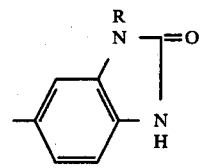

and
R7' designates hydrogen, methyl, methoxy, ethoxy, nitro, ($C_1$–$C_4$-alkyl)-carbonylamino, benzoylamino or hydrogen.

6. Dyestuffs of the formula

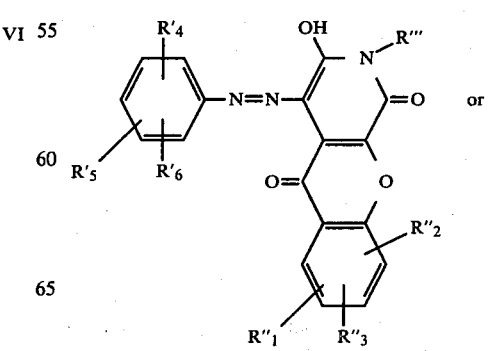

VIII or

-continued

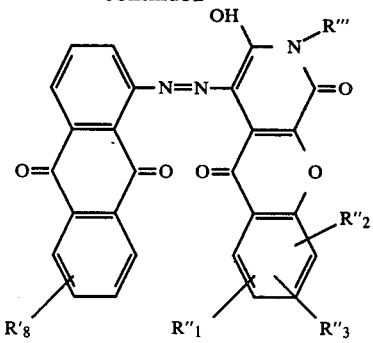

IX wherein
- $R_1''$, $R_2''$ and $R_3''$ represent hydrogen, chlorine, methyl, methoxy, ethoxy, nitro or cyano,
- $R_4'$ and $R_5'$ represent hydrogen, chlorine, bromine, benzoylamino, methoxy, ethoxy, methyl or acetylamino,
- $R_6'$ represents hydrogen, carbamoyl which is optionally substituted by $C_1$–$C_4$-alkyl, phenethyl, benzyl or phenyl, sulphamoyl which is optionally substituted by $C_1$–$C_4$-alkyl, phenethyl, benzyl or phenyl, cyano, nitro or $C_1$–$C_4$-alkoxy-carbonyl,
- $R_8'$ represents hydrogen, acetylamino or benzoylamino and
- $R'''$ represents hydrogen, $C_1$–$C_4$-alkyl, benzyl, phenethyl or phenyl which is optionally substituted by methyl, chlorine, methoxy, ethoxy, phenoxy (which is optionally substituted by chlorine or methyl), carbamoyl, sulphamoyl, acetylamino, benzoylamino or nitro.

7. A dyestuff according to claim 1, wherein A represents the radical of the coupling component of the formula

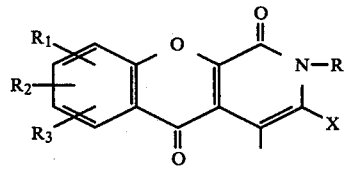

8. A dyestuff according to claim 7, having the formula

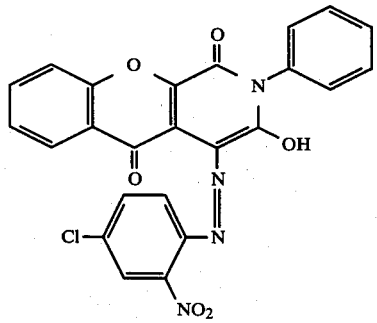

* * * * *